(12) United States Patent
Solberg

(10) Patent No.: US 11,660,468 B2
(45) Date of Patent: May 30, 2023

(54) OPTICAL THERAPEUTIC DEVICE

(71) Applicant: Akulight AS, Kristiansand S (NO)

(72) Inventor: Jan Fredrik Solberg, Kristiansand S (NO)

(73) Assignee: Akulight AS, Kristiansand S (NO)

( * ) Notice: Subject to any disclaimer, the term of this patent is extended or adjusted under 35 U.S.C. 154(b) by 64 days.

(21) Appl. No.: 16/492,063

(22) PCT Filed: Mar. 6, 2018

(86) PCT No.: PCT/NO2018/050056
§ 371 (c)(1),
(2) Date: Sep. 6, 2019

(87) PCT Pub. No.: WO2018/164582
PCT Pub. Date: Sep. 13, 2018

(65) Prior Publication Data
US 2020/0101314 A1    Apr. 2, 2020

(30) Foreign Application Priority Data
Mar. 6, 2017   (NO) .................................. 20170329

(51) Int. Cl.
*A61N 5/06*      (2006.01)

(52) U.S. Cl.
CPC .... *A61N 5/0619* (2013.01); *A61N 2005/0631* (2013.01); *A61N 2005/0632* (2013.01);
(Continued)

(58) Field of Classification Search
CPC ....... A61B 5/06; A61B 5/0619; A61B 18/203; F21L 4/00; A61N 2005/0644
See application file for complete search history.

(56) References Cited

U.S. PATENT DOCUMENTS 1,707,366 A * 4/1929 Pasque ............... A61N 5/06
                                                        601/18
5,161,879 A * 11/1992 McDermott ......... F21L 4/027
                                                        200/60

(Continued)

FOREIGN PATENT DOCUMENTS

DE       44 29 192 A1    2/1996
EP        2735337 A1     5/2014
(Continued)

OTHER PUBLICATIONS

Spherical Lenses, Shanghai Optics.*
(Continued)

*Primary Examiner* — Lynsey C Eiseman
(74) *Attorney, Agent, or Firm* — Knobbe, Martens, Olson & Bear, LLP

(57) ABSTRACT

An optical therapeutic device comprising a front body portion, a light source provided in said front body portion, a spherical, translucent quartz lens provided in front of said light source, a bezel provided on said front body portion and configured to hold said spherical, translucent quartz lens such that a portion of the quartz lens protrudes outside the rim of the bezel. Also described is a method of using the device to apply light stimulation to acupuncture points of a human or animal body and a method for manufacturing the device.

4 Claims, 4 Drawing Sheets

(52) U.S. Cl.
CPC ............. *A61N 2005/0644* (2013.01); *A61N 2005/0651* (2013.01); *A61N 2005/0662* (2013.01)

(56) References Cited

U.S. PATENT DOCUMENTS

| | | | |
|---|---|---|---|
| 5,968,033 A | 10/1999 | Fuller et al. | |
| 6,406,474 B1* | 6/2002 | Neuberger | A61B 18/203 606/3 |
| 6,500,198 B1 | 12/2002 | Southard | |
| 7,883,534 B1 | 2/2011 | Crosby | |
| 9,233,261 B1 | 1/2016 | Crosby | |
| 2007/0002559 A1* | 1/2007 | Uke | F21V 21/406 362/157 |
| 2009/0299236 A1* | 12/2009 | Pryor | A61N 5/0616 601/18 |
| 2009/0299349 A1* | 12/2009 | Kubota | A61N 5/06 606/9 |
| 2012/0065575 A1* | 3/2012 | Loenardi Kader | A61N 1/325 604/20 |
| 2012/0226268 A1* | 9/2012 | Liu | A61N 5/0613 606/9 |
| 2013/0317571 A1* | 11/2013 | Gerlitz | A61N 5/06 607/89 |
| 2015/0360014 A1* | 12/2015 | Decaux | A45D 34/04 604/20 |
| 2017/0136257 A1* | 5/2017 | Jurna | A61N 5/0616 |

FOREIGN PATENT DOCUMENTS

| | | |
|---|---|---|
| JP | H06-319819 A | 11/1994 |
| JP | 2001-112844 A | 4/2001 |

OTHER PUBLICATIONS

Norwegian Search Report for Application No. 20170329, dated Sep. 29, 2017 in 2 pages.
Communication Pursuant to Article 94(3) EPC for European Application No. 18 714 624.6, dated Nov. 23, 2020 in 5 pages.
International Search Report and Written Opinion for PCT Application No. PCT/NO2018/050056, dated Jun. 1, 2018 in 17 pages.

* cited by examiner

OPTICAL THERAPEUTIC DEVICE

CROSS-REFERENCE TO RELATED APPLICATIONS

This application is the U.S. National Phase under 35. U.S.C. § 371 of International Application PCT/NO2018/050056, filed Mar. 6, 2018, which claims priority to Norwegian Patent Application No. 20170329, filed Mar. 6, 2017. The disclosures of the above-described applications are hereby incorporated by reference in their entirety.

TECHNICAL FIELD

The present invention relates to a device for treatment of humans and animals with light. In particular, the invention relates to a device for applying light to specific parts of the body of a human or an animal.

BACKGROUND

A wide range of therapeutic techniques and devices has been developed for non-invasive treatment of human and animal bodies. These range from those based in traditional medicine, such as acupressure and moxibustion, through modern physical therapy and chiropractic, Transcutaneous Electrical Nerve Stimulation (TENS) and Extracorporeal shockwave therapy (ESWT), as well as various forms of therapy based in alternative medicine, often involving magnets, crystals and the like, just to mention a few.

Beneficial properties of various forms of light has been recognized, and various forms of light therapy have been developed, including treatment for various skin conditions, retinal conditions, mood and sleep related conditions, laser acupuncture etc.

The actual beneficial properties of the various therapies and therapeutic devices mentioned above range from well documented to unverified to extremely unlikely. There is therefore a need for non-invasive therapeutic devices that provide a verifiable physiological response in the body of a mammal and at the same time is convenient and user friendly for therapist as well as for the patient.

SUMMARY OF THE DISCLOSURE

The invention relates to an optical therapeutic device with a front body portion, a light source provided in the front body portion, a spherical, translucent quartz lens provided in front of the light source and a bezel provided on the front body portion and configured to hold the spherical, translucent quartz lens such that a portion of the quartz lens protrudes outside the rim of the bezel.

The optical therapeutic device may have a front body portion which is integrally or removably coupled to a rear body portion. In some embodiments the rear body portion has an elongate shape. Other embodiments include a rear body portion has a substantially spherical shape. Other shapes of the front and rear body portions are possible within the scope of the invention.

The spherical, translucent quartz may be transparent. In some embodiments the spherical, translucent quartz lens is made of clear rock crystal.

The quartz lens is not limited to any specific size. In some embodiments it is between 8 mm and 12 mm in diameter, for example 10 mm, and the quartz lens may protrude between 2 mm and 4 mm outside the rim of the bezel, for example 3 mm. Other sizes may be contemplated, but may be limited by the desired size of the device as well as the properties of the lights source.

The rim of the bezel and the protruding portion of the quartz lens are in some embodiments of the invention adapted to rest against the skin of a patient at the location of an acupuncture point during treatment.

According to an aspect of the invention, a method for applying light stimulation at acupuncture points of a human or animal body, comprises providing an optical therapeutic device with a front body portion including a light source and a spherical, translucent quartz lens provided in front of the light source, activating the optical therapeutic device such that light passes from the light source and through the translucent quartz lens, resting or pressing a portion of the quartz lens protruding from the front body portion against an acupuncture point thus stimulating the acupuncture point with light that has passed through the translucent quartz lens, and repeating the step of stimulating the same or an additional acupuncture point with light that has passed through the translucent quartz lens in accordance with a prescribed schedule for treatment.

According to another aspect of the invention, a method for manufacturing an optical therapeutic device, comprises providing a body with an elongate front body portion, mounting a light source in the elongate front body portion directed out of the front body portion, providing a spherical, translucent quartz lens provided in front of the light source, and attaching a bezel on the front body portion such that it holds the spherical, translucent quartz lens while allowing a portion of the quartz lens to protrude outside the rim of the bezel.

DETAILED DESCRIPTION

The present invention relates to a light therapy device and in particular to a device for applying light to specific parts of the body.

Figure 1:
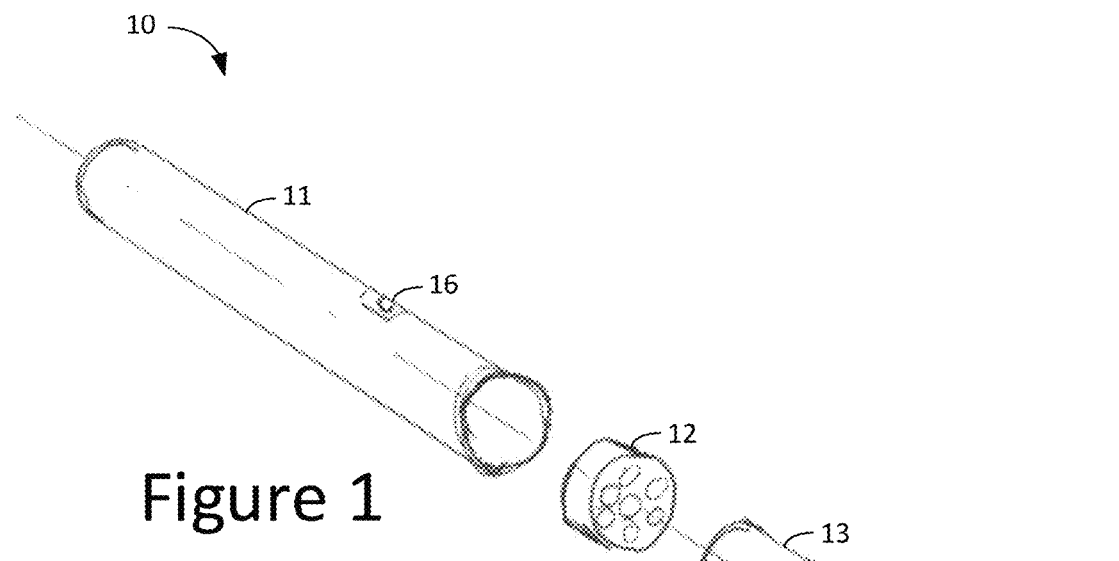
FIG. 1 is an exploded perspective view of a device according to the invention.

Reference is first made to FIG. 1, wherein a light therapy device, or optical therapeutic apparatus, according to the present invention is illustrated in a perspective exploded view. The device 10 is substantially shaped and constructed like a barrel type flashlight with a tubular body 11, which may be configured to hold batteries for powering the light source, as well as the necessary connectors, wires and switches (not shown).

The front end of the tubular body 11 may be provided with a slightly larger inner diameter configured to receive the light source 12. Other alternatives for fitting, holding or securing the light source includes threads, screws, glue, bayonet mount and other methods known to those with skill in the art.

The light source may be a LED light source, for example a high intensity white LED capable of providing approximately 30 lux.

A spacer 13 is provided in front of the light source 12. The spacer 13 is substantially a cylinder, which is configured to ensure that the appropriate distance is provided between the light source 12 and the lens 14. The end of the spacer that faces the light source is substantially flat, allowing the spacer to rest against the surface of the light source 12 or the tubular body 11. The end facing the lens 14 may be provided with an end that is angled inward, providing a seat for the lens 14.

The lens 14 is a sphere made of rock crystal, i.e. a pure, colorless quartz. The lens may be made in various sizes and the invention is not limited to any specific size. A size of approximately 10 mm in diameter, for example between 8 mm and 12 mm in diameter, and with corresponding dimensions for the remaining components, will provide a device with dimensions that are comfortable to work with for an operator. The term "spherical" is not intended to be interpreted strictly mathematically, and minor deviations from a perfect sphere will, of course, be within the scope of the invention. Deviations from a perfect sphere may include deviations in general shape, such as slightly spheroidal shapes, as well as smaller local deviations in the form of holes, notches or grooves for facilitating the holding of the lens in its position.

At the end of the device a bezel 15 is holding the lens 14 in place. The bezel may be screwed on to the tubular body 11 by threads provided on the bezel 15 and the tubular body 11. However, other ways of attaching the bezel may be contemplated, including bayonet mount, glue, welding or soldering, as well as other methods known in the art.

The bezel may have an opening that allows the spherical lens protrude approximately 3 mm, for example between 2 mm and 4 mm outside the rim of the bezel. The bezel may have a smooth surface such that the bezel 15 and the protruding portion of the lens 14 is well adapted to rest against the skin of a patient at the location of an acupuncture point during treatment.

A switch 16 may be provided in order to turn the device on and off by connecting and disconnecting the light source 12 from a power source. The power source (not shown) may be one or more batteries provided inside the tubular body 11.

Other assemblies may, of course, be contemplated within the scope of the invention. In particular, the various parts may be constructed from several parts, or they may have shapes that deviate from this exemplary embodiment.

Figure 2:
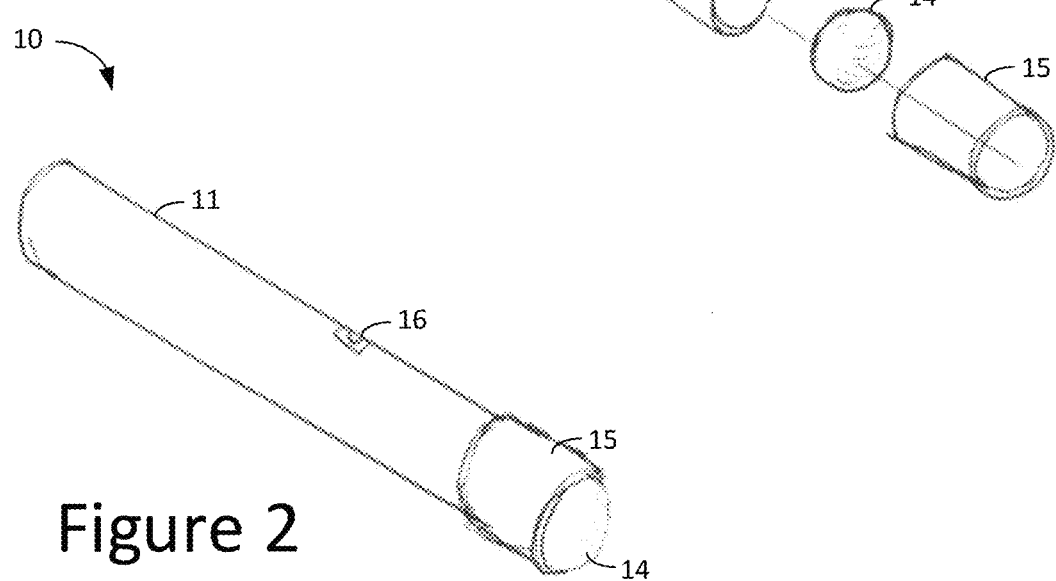
FIG. 2 is an assembled perspective view of the same device.

FIG. 2 shows the same device in an assembled perspective view.

An experiment was performed in order to determine physiological effects on humans from use of a device according to the invention. The experiment was performed on healthy subjects between 18 and 50 years of age, and was designed to measure whether a device according to the invention had any measurable effect on blood pressure, heart rate, oxygen saturation or EKG.

The experiment was designed as a double blind experiment. The subjects were unaware of any technical features or presumed physiological effects of its use, and the measurements were performed by a medical secretary who similarly had no knowledge of the device.

The subjects arrived and were allowed to rest for 20 minutes prior to the experiment, placed on an examination table and prepared for the examination.

The first measurement to be performed was determination of baseline. Blood pressure, heart rate, oxygen saturation and EKG were measured.

After a 10 minute rest, the subjects were then exposed to placebo treatment, in which "treatment" was performed without light. The "treatment" was directed toward neck and leg, and lasted for approximately 20 minutes. During this period several measurements of blood pressure, heart rate, oxygen saturation and EKG were performed.

Subsequent to this second set of measurements, a third set of measurements were performed during exposure of the subjects to light from a device according to the invention. In particular, the device was directed toward the neck and the medial malleolus. Again repeated measurements were performed during and after the exposure during a period of approximately 20 minutes.

The tests revealed that blood pressure and heart rate fell for all subjects from baseline to the second and the third measurement. Oxygen saturation was relatively stable and did not change significantly. Furthermore, and importantly, there was a minor reduction in the results from the second to the third measurement. Again, oxygen saturation was stable and did not change significantly.

No change in the electrophysiology of the heart during the tests, as it was observed that EKG was constant in all subjects for all three measurements, except minor changes in frequency associated with the reduction in heart rate.

The following is a summary of the results when comparing treatment with a placebo with treatment with the device according to the invention.

Figure 3:
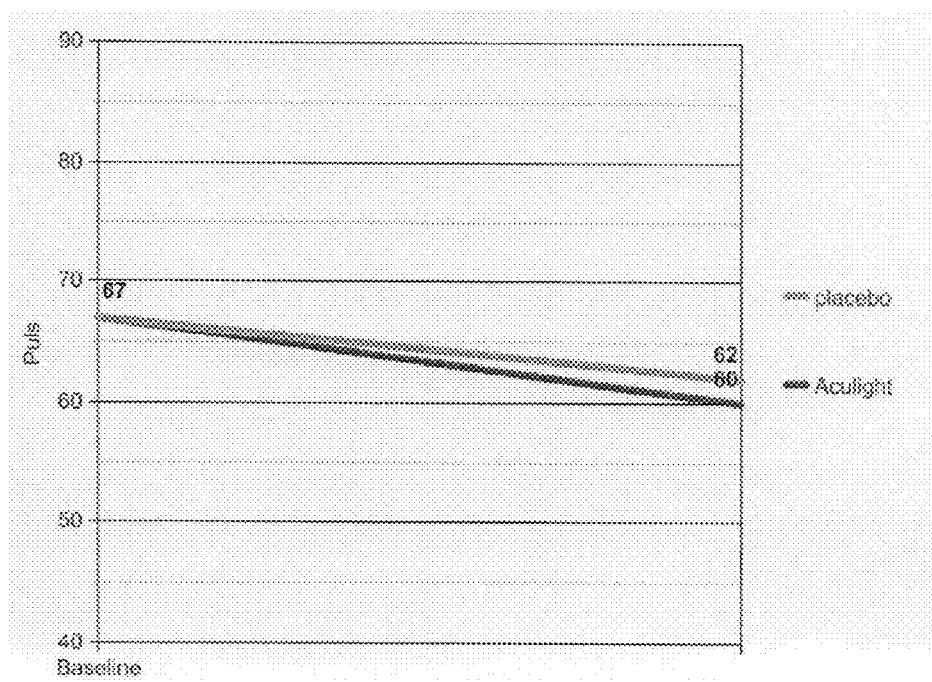
FIG. 3 is a graph showing the difference between treatment with a placebo and treatment with a device according to the invention on the heart rate of test subjects.
Figure 4:
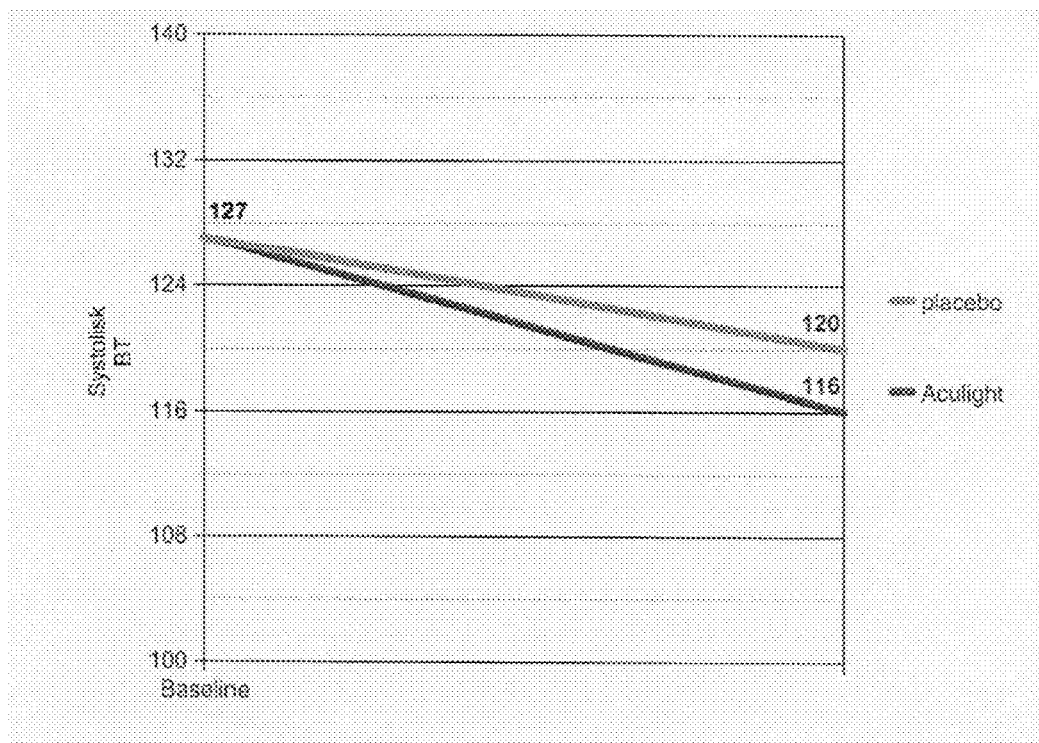
FIG. 4 is a graph showing the difference between treatment with a placebo and treatment with a device according to the invention on the blood pressure of test subjects.

Blood pressure reduction: 3.3%
Heart rate reduction: 3.2%
Oxygen saturation: Substantially constant
EKG: Substantially constant The results are illustrated in FIG. 3 and FIG. 4. FIG. 3 shows the fall in heart rate from a baseline heart rate of 67 to a placebo heart rate of 62 and from a baseline heart rate of 67 to a heart rate of 60 after treatment with the invented device. FIG. 4 shows the fall in systolic blood pressure from a baseline of 127 to a placebo of 120 and a corresponding fall from baseline 127 to 116 after treatment with the invented device.

It was concluded that while oxygen saturation and electrophysiology of the heart remained unchanged, use of the invention was associated with reductions in blood pressure and heart rate compared with use of a placebo.

Figure 5:
FIG. 5 is a cross sectional view of a device according to an embodiments of the invention.

Reference is now made to FIG. 5, which shows a more detailed view of an embodiment of the invention.

This cross sectional view of a device 10 according to the invention shows the tubular body 11 and the bezel 15 which is screwed or otherwise attached at its end. Inside the bezel the light source 12, the spacer 13 and the lens 14 are positioned and held in place between the end of the tubular body 11 and the narrowing end of the bezel 15. The body 11 may include sufficient space for a battery, but a device 10 according to the invention may also be configured with external connectors allowing it to be connected to an external powers source. Wires or leads connecting the switch 16 and the light source 12 to the power source may be integrated in or attached to the inner surface of the body 11. Internal wiring of flashlights and similar devices are well known in the art and can easily be adapted to a device according to the invention, and will therefore not be explained in further detail herein.

Figure 6:
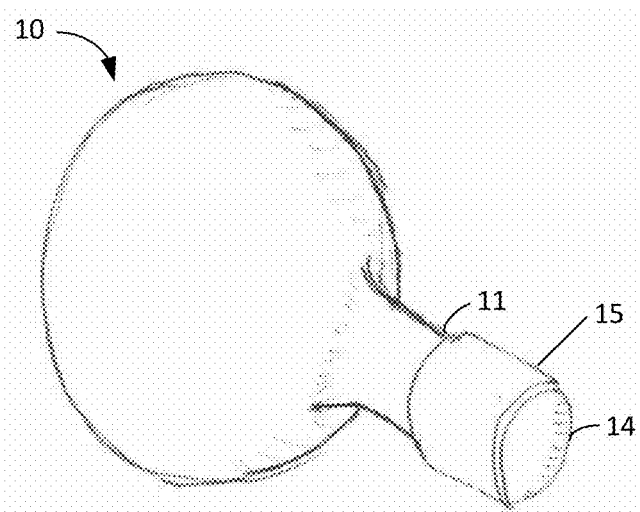
FIG. 6 is a perspective view of another embodiment of the invention.

In the embodiments described above, the device 10 has the general shape of a pen due to the tubular shape of the tubular body 11. However, other shapes are consistent with the principles of the invention. One example is illustrated in FIG. 6, which shows an embodiment of a device 10 according to the invention wherein the body 11 has a front portion that is elongate, for example tubular as described above. However, the body may include a rear body part which may be of the same elongate shape, but which may also have a wider shape, for example a substantially spherical shape.

Figure 7A:
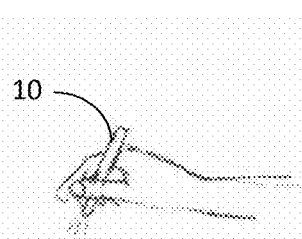
FIGS. 7a and 7b illustrate how different embodiments of the invention may be held by an operator.
Figure 7B:
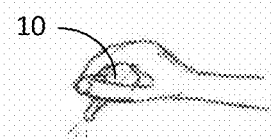

As such, a first embodiment or class of embodiments comprise an elongate shape substantially from one end to the other, suitable for being held in a pen like grip by an operator. This is illustrated in FIG. 7*a*. A second embodiment or class of embodiments has an elongate front portion with the light source 12, lens 14 and bezel 15 arranged at its end, but with a substantially spherical rear portion which is more suitable for being held in the palm of a hand, much like a door knob or a computer mouse, as shown in FIG. 7*b*.

Substantially spherical as used herein signifies a shape that has the appearance of a sphere, but which may deviate from a perfect sphere, for example by being egg shaped, flattened or drop shaped. In any case, a shape deviating from a perfect sphere by less than 25% in maximum vs minimum distance from the center of the rear part of the body falls within what this disclosure refers to as substantially spherical. Additional shapes may also be contemplated without departing from the scope of the invention. For example, the rear body part may be ergonomically shaped in order to fit comfortably inside the palm of the hand of an operator. It may also be contemplated to give the device a shape with cross sectional dimensions that vary along the length of the device and that have different cross sectional shapes (e.g. substantially triangular).

The body 11 of the device 10 may be made of a number of different materials, including steel, aluminum and various plastics.

A method of manufacturing an optical therapeutic device according to the invention may include providing a body with an elongate front body portion, for example by machining or molding. In a next step a light source may be mounted in the elongate front body portion such that it is directed outwards, or forward, with respect to the front body portion. Following this a spherical, translucent quartz lens can be provided in front of the light source. Optionally a spacer is mounted between the light source and the lens. Finally, a bezel is attached on the front body portion such that it holds the spherical, translucent quartz lens while allowing a portion of the quartz lens to protrude outside the rim of the bezel.

A device according to the invention may have a number of uses. One possible use is a method for applying light stimulation at acupuncture points of a human or animal body. According to this method, an optical therapeutic device with a front body portion including a light source and a spherical, translucent quartz lens provided in front of the light source is used. The optical therapeutic device is activated such that light passes from the light source and through the translucent quartz lens. The device is then positioned such that a portion of the quartz lens protruding from the front body portion is resting or pressing against an acupuncture point, thus stimulating the acupuncture point with light that has passed through the translucent quartz lens. This can be repeated such that the same or an additional acupuncture point is stimulated with light that has passed through the translucent quartz lens in accordance with a prescribed schedule for treatment.

What is claimed is:

1. An optical therapeutic device comprising:
   a tubular body;
   a light source, wherein said light source is a white LED light source capable of providing approximately 30 lux;
   a power source comprising one or more batteries provided inside the tubular body;
   a bezel;
   a spherical quartz lens provided in front of said light source, wherein said spherical quartz lens:
     is transparent,
     is made of clear rock crystal,
     is between 8 mm and 12 mm in diameter, and protrudes between 2 mm and 4 mm outside a rim of the bezel;
   wherein the bezel is provided on said tubular body and is configured to hold said spherical quartz lens and the light source such that a portion of the spherical quartz lens protrudes outside a rim of the bezel, wherein the bezel is removably coupled to the tubular body; and
   a spacer formed as a cylinder allowing the spacer to rest against the surface of the light source or tubular body, wherein the spacer comprises a first end facing the spherical quartz lens that is angled inward, thereby providing a seat for the spherical quartz lens, and a second end facing the light source that is substantially flat.

2. The optical therapeutic device according to claim 1, wherein said the tubular body has an elongate shape.

3. The optical therapeutic device according to claim 1, wherein said the tubular body has a substantially spherical shape.

4. The optical therapeutic device according to claim 1, wherein the rim of the bezel and the protruding portion of the spherical quartz lens are adapted to rest against the skin of a patient at the location of an acupuncture point during treatment.

* * * * *